United States Patent
Shibahara et al.

(10) Patent No.: US 11,898,923 B2
(45) Date of Patent: Feb. 13, 2024

(54) MEASURING METHOD OF RESIDUAL STRESS DISTRIBUTION, CALCULATING METHOD OF SAME, AND PROGRAM

(71) Applicant: UNIVERSITY PUBLIC CORPORATION OSAKA, Osaka (JP)

(72) Inventors: Masakazu Shibahara, Sakai (JP); Kazuki Ikushima, Sakai (JP); Atsushi Kawahara, Sakai (JP); Yoshitaka Kawajiri, Sakai (JP); Yui Okimi, Sakai (JP)

(73) Assignee: UNIVERSITY PUBLIC CORPORATION OSAKA, Osaka (JP)

( * ) Notice: Subject to any disclaimer, the term of this patent is extended or adjusted under 35 U.S.C. 154(b) by 426 days.

(21) Appl. No.: 17/274,696

(22) PCT Filed: Aug. 22, 2019

(86) PCT No.: PCT/JP2019/032870
§ 371 (c)(1),
(2) Date: Mar. 9, 2021

(87) PCT Pub. No.: WO2020/054347
PCT Pub. Date: Mar. 19, 2020

(65) Prior Publication Data
US 2022/0018724 A1 Jan. 20, 2022

(30) Foreign Application Priority Data
Sep. 11, 2018 (JP) ................................. 2018-169714

(51) Int. Cl.
*G01N 33/207* (2019.01)
*G01L 5/00* (2006.01)
*G06F 30/23* (2020.01)

(52) U.S. Cl.
CPC .......... *G01L 5/0047* (2013.01); *G01N 33/207* (2019.01); *G06F 30/23* (2020.01)

(58) Field of Classification Search
CPC ..... G01L 5/0047; G01N 33/207; G06F 30/23; G06F 30/15; G06F 30/17; G06F 30/20; G06F 2119/14
See application file for complete search history.

(56) References Cited

U.S. PATENT DOCUMENTS 6,470,756 B1   10/2002  Prime
9,868,145 B2 *  1/2018  Suzuki ................... B21D 22/00
(Continued)

FOREIGN PATENT DOCUMENTS

DE    102005008281 A1   8/2006
JP    2015-504170 A     2/2015
JP    2017-156263 A     9/2017

OTHER PUBLICATIONS

Kawajiri, Yoshitaka, et al. "Measurement of Welding Residual Stress Using Contour Method," Lecture Proceeding of 2017 symposium on Welding Mechanics and Design, Dec. 5, 2017, pp. 341-348 (see ISR, no translation available).
(Continued)

*Primary Examiner* — Tung S Lau
(74) *Attorney, Agent, or Firm* — Stites & Harbison, PLLC; Jeffrey A. Haeberlin

(57) ABSTRACT

A residual stress distribution measuring method of the present invention is characterized by comprising:
by using an analytical model in which a cut-surface is interpolated to a cross section of a metal member, the step of calculating a residual force vector that is a sum of a load vector acting on a first metal piece at the cut-surface and a load vector acting on a second metal piece at the cut-surface;
the step of calculating, as a modified displacement vector, an amount of movement at the cross section by interpolating the residual force vector as a forced load to the cross section of an analytical model of the metal member;
by using an analytical model having the shape of a cut-surface of a measured first or second metal piece, the step of modifying the shape of the cut-surface of the first or the second metal piece on the basis of the calculated modified displacement vector; and
by using the analytical model in which the shape of the cut-surface of the first or the second metal piece is modified, the step of calculating a residual stress distribution at the cross section by interpolating a forced displacement to the analytical model.

5 Claims, 5 Drawing Sheets

(56) References Cited

U.S. PATENT DOCUMENTS

| | | | |
|---|---|---|---|
| 9,934,339 B2* | 4/2018 | Madhavan | G06F 30/20 |
| 10,684,392 B2* | 6/2020 | Mookanahallipatna Ramasesha | G06F 30/20 |
| 2007/0251327 A1* | 11/2007 | Broene | G01N 3/32 73/769 |
| 2008/0294397 A1* | 11/2008 | Ohnishi | G06F 30/23 703/2 |
| 2015/0025815 A1 | 1/2015 | Sebastiani et al. | |
| 2016/0334544 A1* | 11/2016 | Mookanahallipatna Ramasesha | G01V 99/005 |

OTHER PUBLICATIONS

Japan Patent Office, International Search Report, International phase of current application (application No. PCT/JP2019/032870), dated Nov. 12, 2019.

* cited by examiner

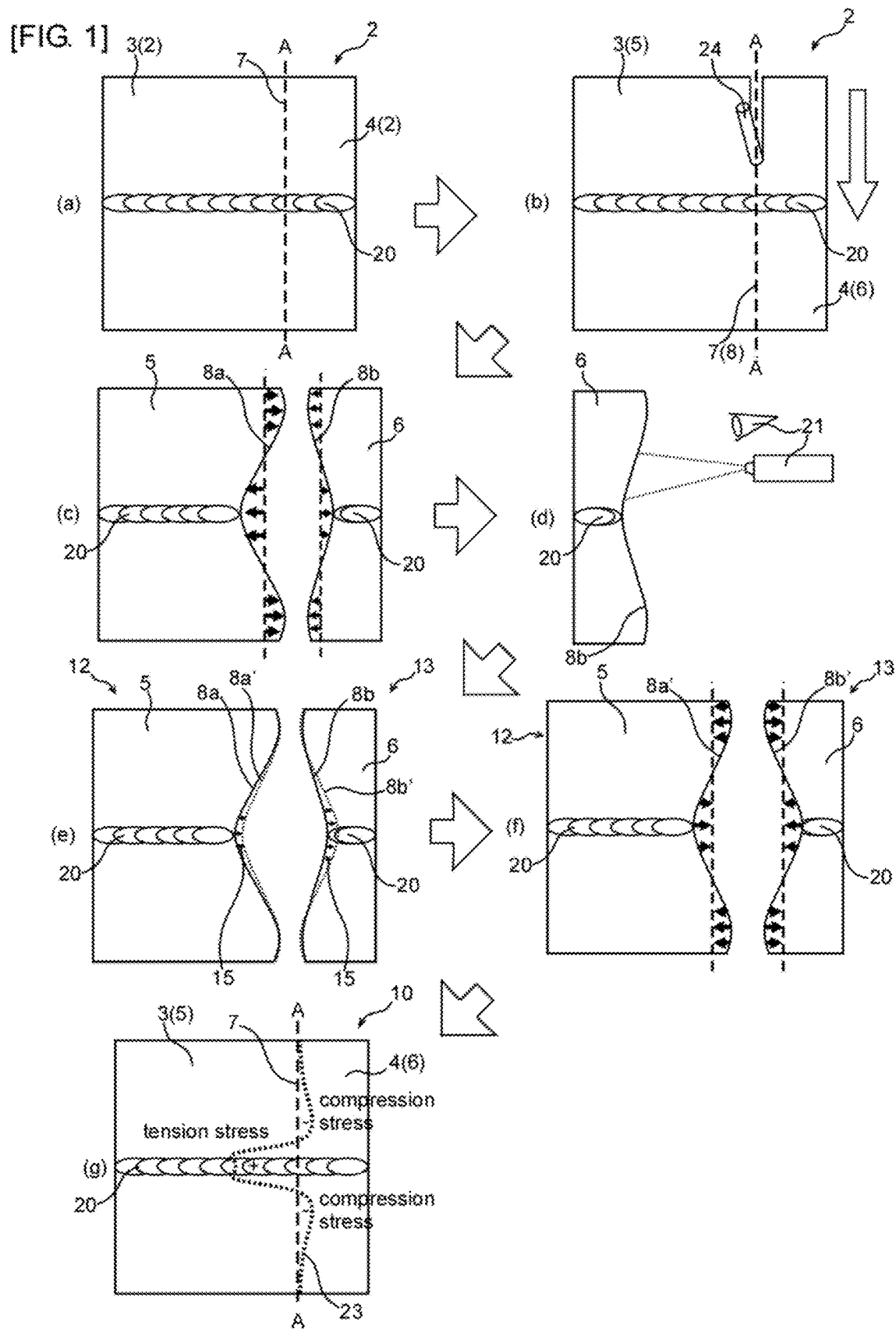

[FIG. 2]
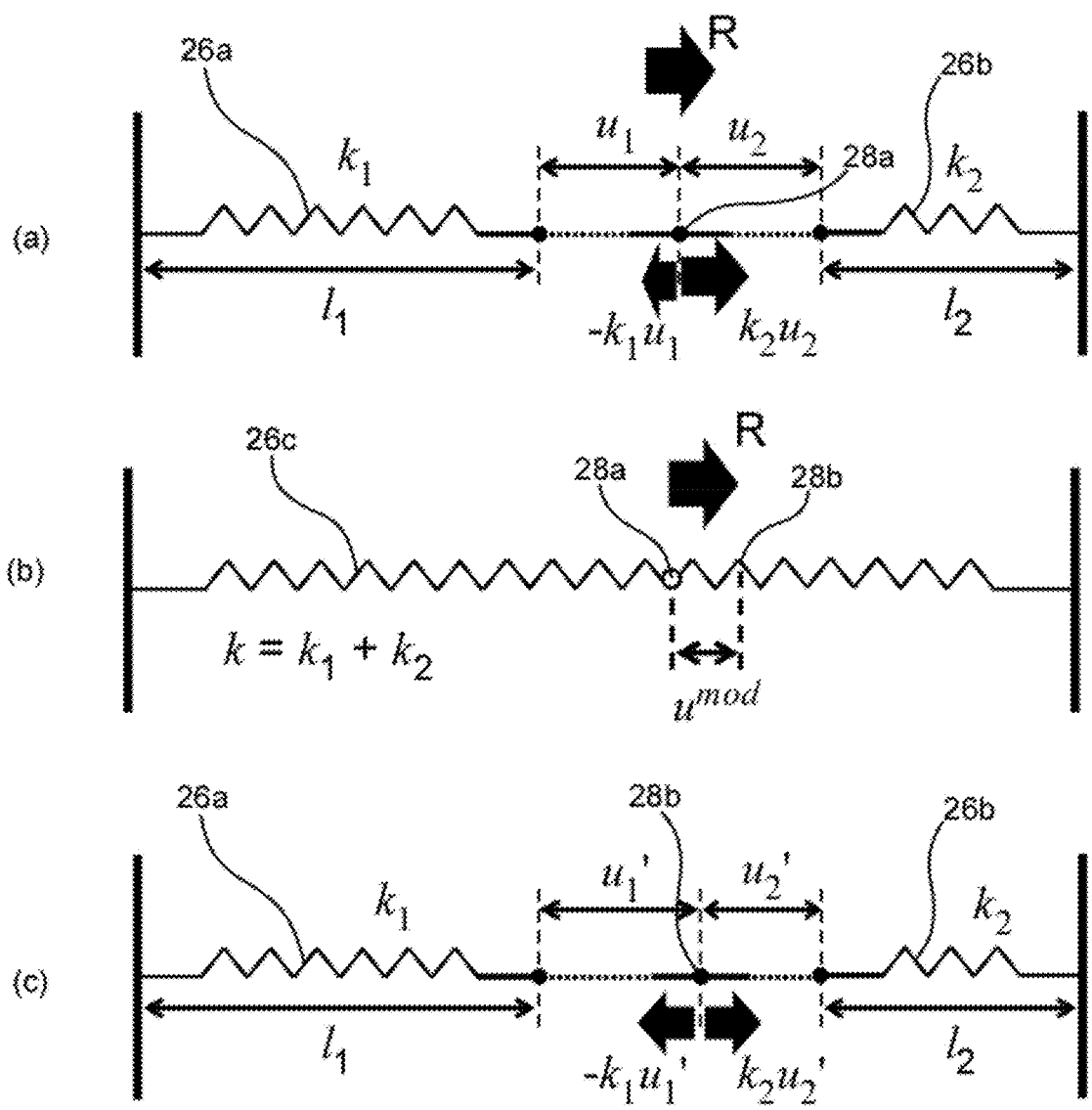

[FIG. 3]
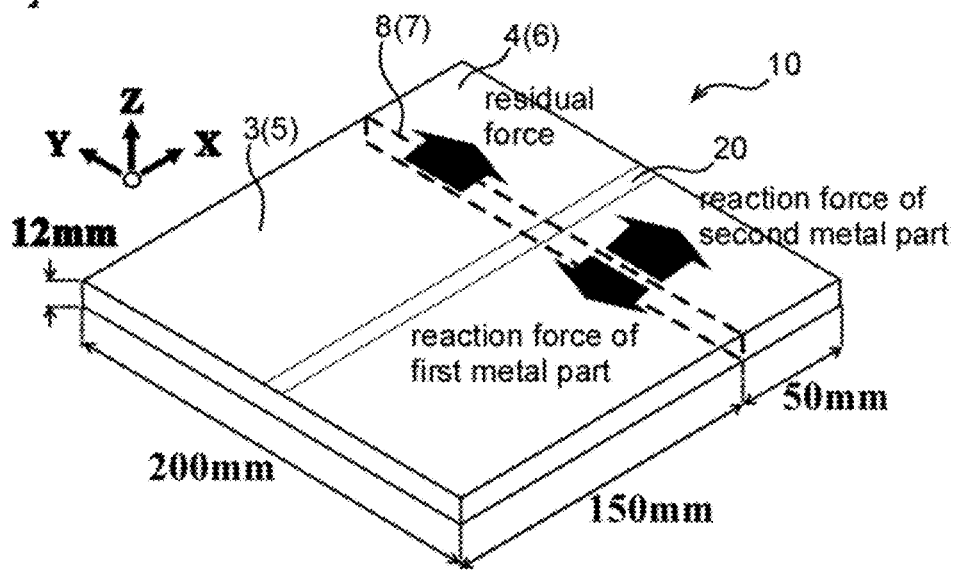
[FIG. 4]
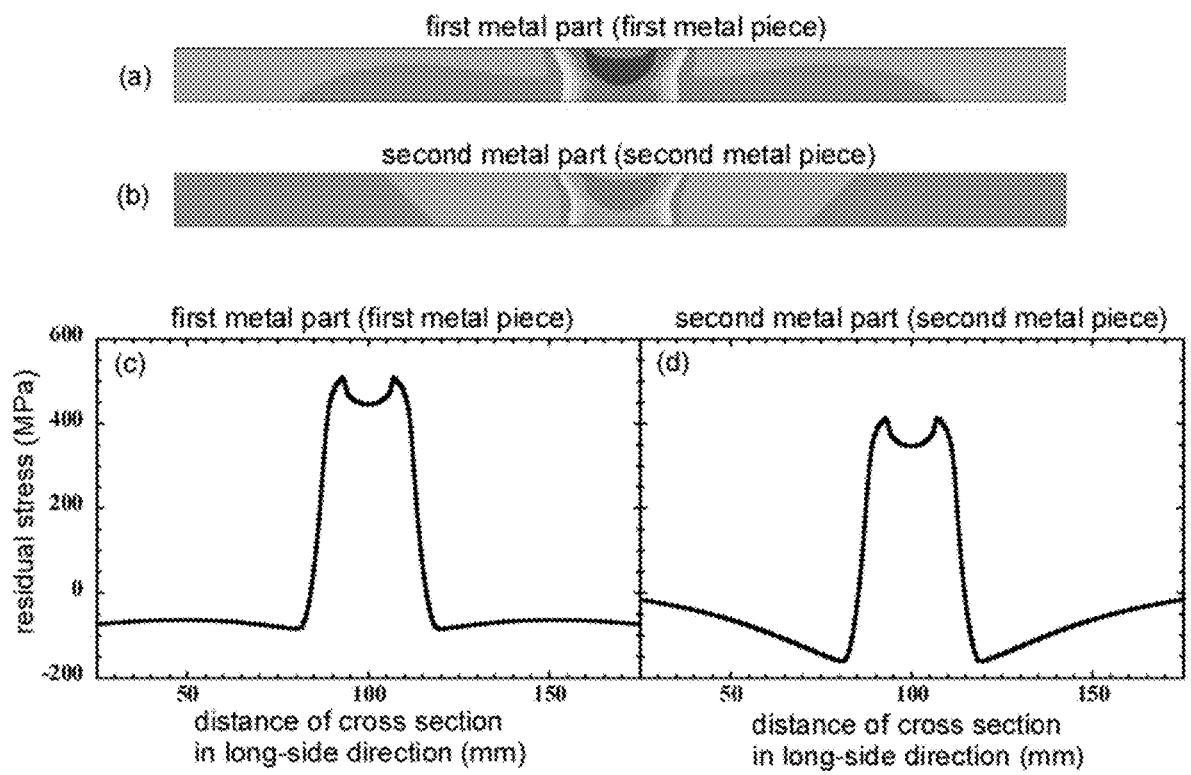

[FIG. 5]
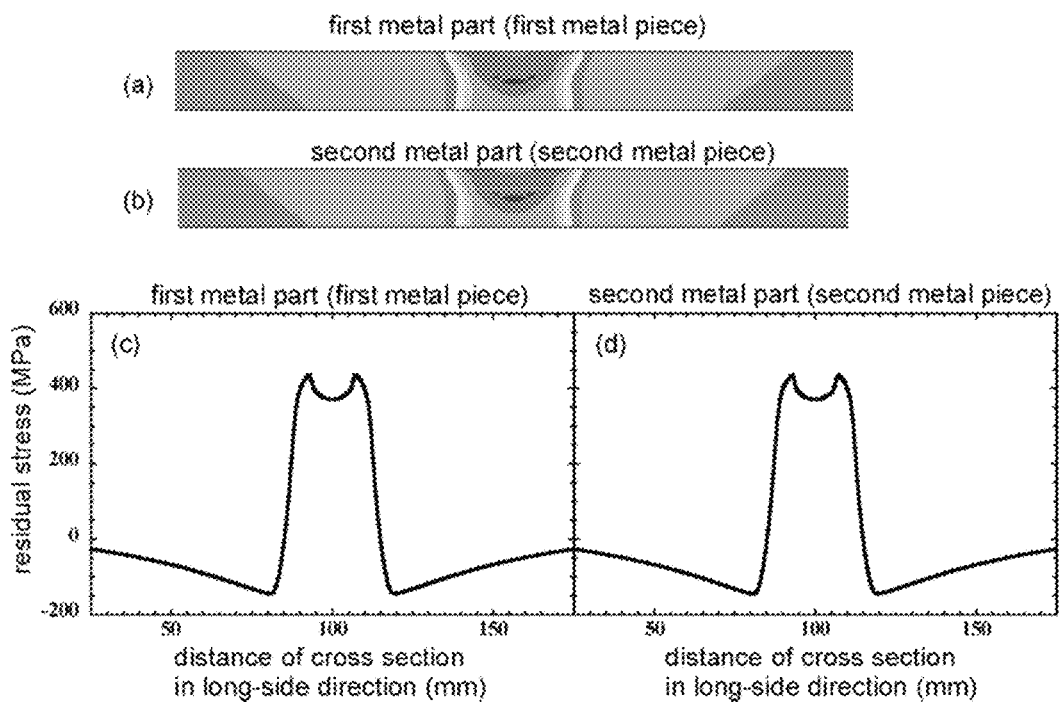
[FIG. 6]
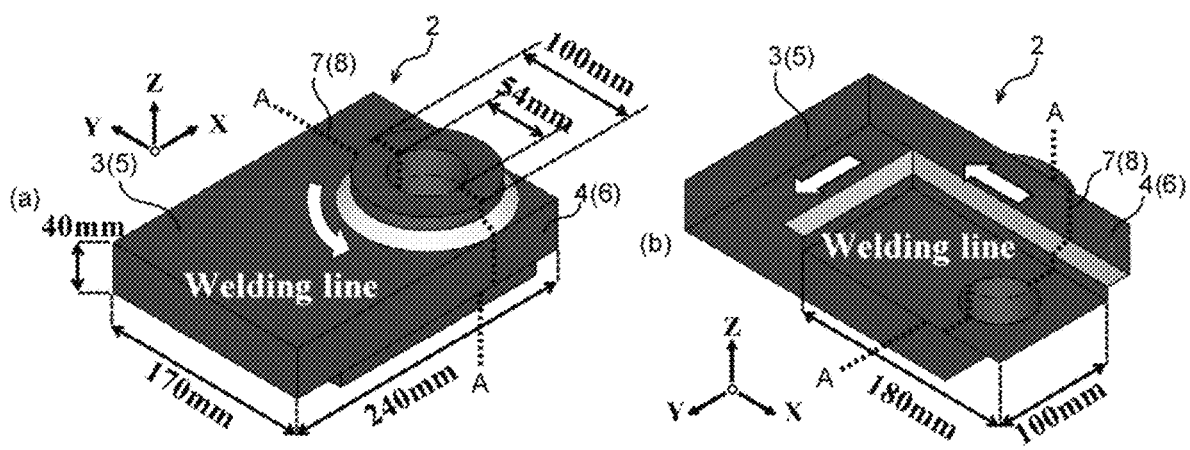

[FIG. 7]
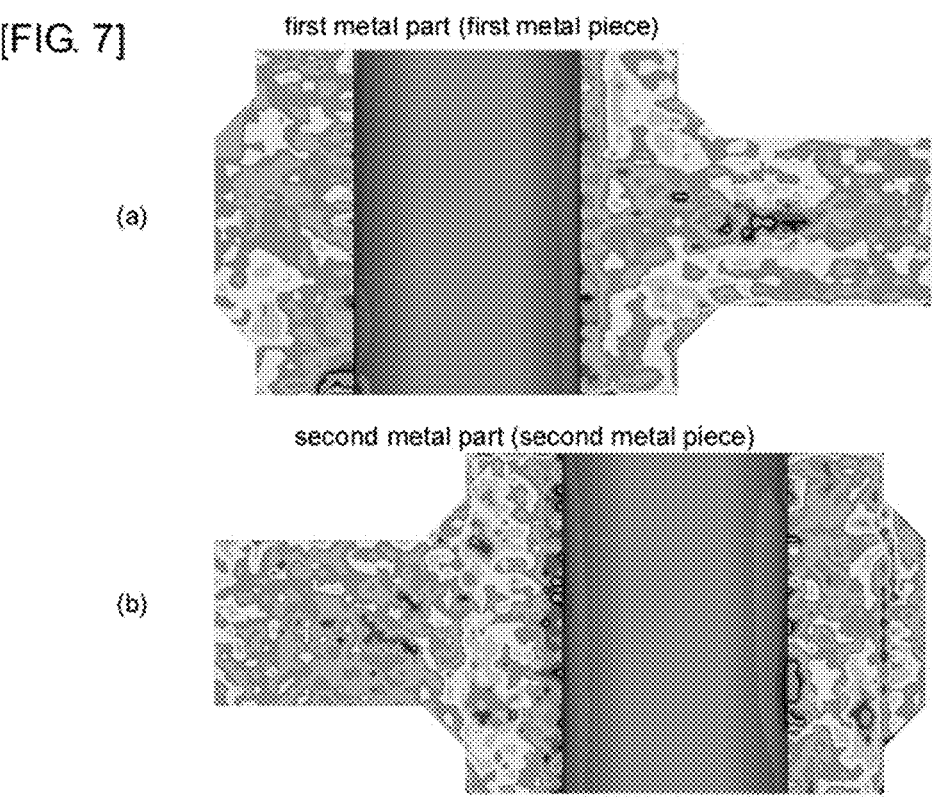
(a) first metal part (first metal piece)
(b) second metal part (second metal piece)
[FIG. 8]
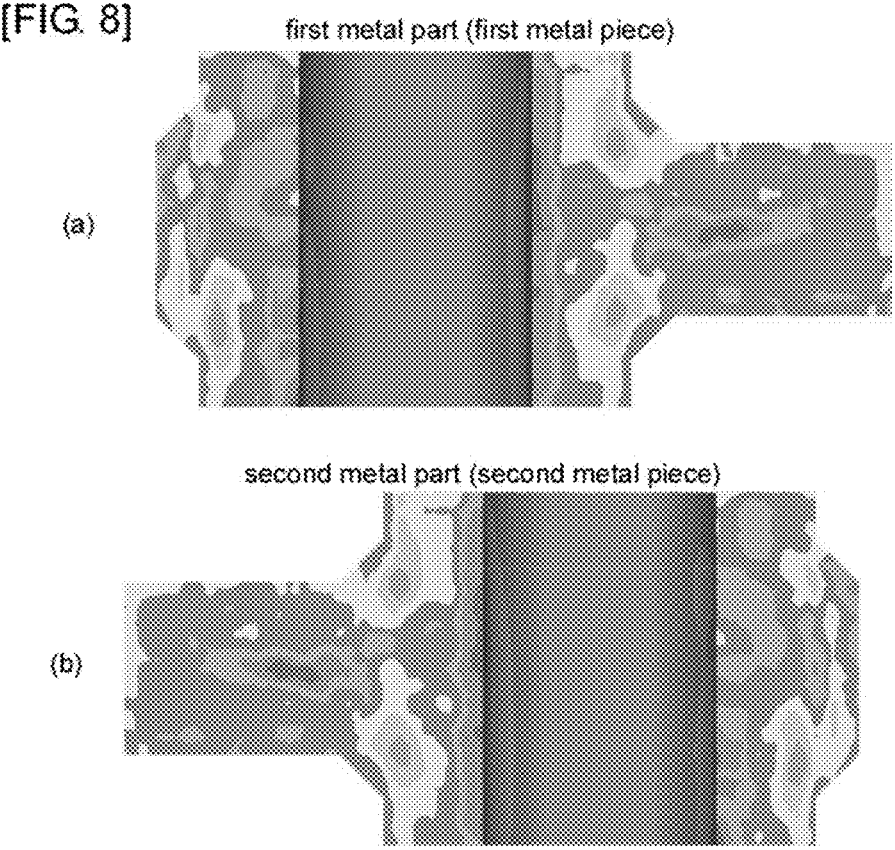
(a) first metal part (first metal piece)
(b) second metal part (second metal piece)

MEASURING METHOD OF RESIDUAL STRESS DISTRIBUTION, CALCULATING METHOD OF SAME, AND PROGRAM

TECHNICAL FIELD

The present invention relates to a measuring method of a residual stress distribution, a calculating method of the same, and a program.

BACKGROUND ART

In recent years, building large structural objects, as typified by marine vessels and bridges, inevitably requires a process of joining members together upon putting a finish on the members, thereby making joining techniques absolutely indispensable. Of the joining techniques, a technique that has been widely used is welding because of its simplicity and the like. However, the welding may naturally cause high residual tensile stress in the vicinity of a welded area during the welding process, which is considered to be a cause of fatigue fracture, stress corrosion cracking (SCC), and sometimes even brittle fracture. Additionally, residual compressive stress is generated to equilibrate this residual tensile stress; and the residual compressive stress may cause buckling deformation of the member such as a thin plate, possibly causing a significant impact on an assembly process. These stresses are generally referred to as weld residual stresses, and it is very important for the welding process to evaluate a residual stress distribution in the vicinity of the welded area.

A contour method is a low-cost and simple method for residual stress measurement inside a member. Under the contour method, the member to be measured is cut and divided into two pieces; and an amount of elastic deformation of a cut-surface of the member is measured that is developed when residual stress is released; and then a residual stress distribution at the entire cut-surface is calculated based upon the measurement results (see, for example, PTL 1).

CITATION LIST

Patent Literature

PTL 1: U.S. Pat. No. 6,470,756 B1

SUMMARY OF INVENTION

Technical Problem

Under the contour method, it is necessary to average cut-surface shapes of the halved member and remove any measurement roughness caused by scratches on the cut-surface. However, this averaging does not exactly hold without the assumption that the two pieces of the cut member are equal in rigidity. For example, if a homogeneous member is cut exactly symmetrically, this assumption is satisfied; however, if an asymmetric structure is cut, or if a structure is not divided precisely into two pieces at a time of cutting the structure, the above assumption is not satisfied. To measure residual stress of a large steel structure with complex shapes, such as a marine vessel or a bridge, it is extremely difficult to symmetrically cut off a member to be measured so as to make two pieces of the member equal in rigidity. Therefore, it is desired to upgrade the contour method so that residual stress measurement can be performed even when the member is cut off asymmetrically.

The present invention was devised in view of such circumstances, and provides a residual stress distribution measuring method that enables calculation of a residual stress distribution even when a member is cut off asymmetrically.

Solution to Problem

The present invention provides a measuring method for measuring a residual stress distribution at a cross section between a first metal part and a second metal part of a metal member, the measuring method being characterized by comprising:

the step of cutting the metal member at the cross section in such a way that the first metal part is cut off and becomes a first metal piece, and the second metal part is cut off and becomes a second metal piece;

the step of measuring a shape of a cut-surface of the first metal piece or a shape of a cut-surface of the second metal piece;

by using an analytical model in which a cut-surface is interpolated to the cross section of the metal member, the step of calculating a residual force vector that is a sum of a load vector acting on the first metal piece at the cut-surface and a load vector acting on the second metal piece at the cut-surface;

the step of calculating, as a modified displacement vector, an amount of movement at the cross section by interpolating the residual force vector as a forced load to the cross section of an analytical model of the metal member;

by using an analytical model having the shape of the cut-surface of the measured first metal piece or an analytical model having the shape of the cut-surface of the measured second metal piece, the step of modifying the shape of the cut-surface of the first metal piece or the shape of the cut-surface of the second metal piece on the basis of the calculated modified displacement vector; and by using the analytical model in which the shape of the cut-surface of the first metal piece is modified or the analytical model in which the shape of the cut-surface of the second metal piece is modified, the step of calculating a residual stress distribution at the cross section by interpolating a forced displacement to the analytical model.

Advantageous Effects of Invention

The present invention is capable of modifying the shape of the cut-surface by using the amount of movement (modified displacement vector) calculated by interpolating the residual force vector as the forced load to the cross section and thus capable of measuring the residual stress distribution at the cross section between the first metal piece and the second metal piece that are asymmetrical to each other.

BRIEF DESCRIPTION OF DRAWINGS

FIG. 1 shows explanatory diagrams of a residual stress distribution measuring method in accordance with an Embodiment of the present invention.

FIG. 2 shows explanatory diagrams of a residual stress distribution measuring method in accordance with the Embodiment of the present invention.

FIG. 3 shows an analytical model of a metal member to be used for the residual stress distribution measuring method in accordance with the Embodiment of the present invention.

FIG. 4(a) and FIG. 4(c) show a residual stress distribution calculated by a traditional contour method using a cut-surface shape of a first metal piece; and FIG. 4(b) and FIG. 4(d) show a residual stress distribution calculated by the traditional contour method using a cut-surface shape of a second metal piece.

FIG. 5(a) and FIG. 5(c) show a residual stress distribution calculated by a modified contour method of the present invention using a modified cut-surface shape of a first metal piece; and FIG. 5(b) and FIG. 5(d) show a residual stress distribution calculated by the modified contour method of the present invention using a modified cut-surface shape of a second metal piece.

FIG. 6 shows diagrammatic perspective views of a test object used for a residual stress distribution measurement.

FIG. 7(a) shows a residual stress distribution calculated by the traditional contour method using the cut-surface shape of the first metal piece; and FIG. 7(b) shows a residual stress distribution calculated by the traditional contour method using the cut-surface shape of the second metal piece.

FIG. 8(a) shows a residual stress distribution calculated by the modified contour method of the present invention using the modified cut-surface shape of the first metal piece; and FIG. 8(b) shows a residual stress distribution calculated by the modified contour method of the present invention using the modified cut-surface shape of the second metal piece.

DESCRIPTION OF EMBODIMENTS

A measuring method of the present invention for measuring a residual stress distribution at a cross section between a first metal part and a second metal part of a metal member is characterized by comprising:

the step of cutting the metal member at the cross section in such a way that the first metal part is cut off and becomes a first metal piece, and the second metal part is cut off and becomes a second metal piece; the step of measuring a shape of a cut-surface of the first metal piece or a shape of a cut-surface of the second metal piece;

by using an analytical model in which a cut-surface is interpolated to the cross section of the metal member, the step of calculating a residual force vector that is a sum of a load vector acting on the first metal piece at the cut-surface and a load vector acting on the second metal piece at the cut-surface;

the step of calculating, as a modified displacement vector, an amount of movement at the cross section by interpolating the residual force vector as a forced load to the cross section of an analytical model of the metal member;

by using an analytical model having the shape of the cut-surface of the measured first metal piece or an analytical model having the shape of the cut-surface of the measured second metal piece, the step of modifying the shape of the cut-surface of the first metal piece or the shape of the cut-surface of the second metal piece on the basis of the calculated modified displacement vector; and by using the analytical model in which the shape of the cut-surface of the first metal piece is modified or the analytical model in which the shape of the cut-surface of the second metal piece is modified, the step of calculating a residual stress distribution at the cross section by interpolating a forced displacement to the analytical model.

It is desirable that the step of calculating the residual stress distribution should be the step of calculating the residual stress distribution at the cross section by interpolating the forced displacement to the analytical model by using an elasticity analysis.

The present invention also provides a calculating method for calculating a residual stress distribution based upon a structural analysis by a finite element method at a cross section between a first metal part and a second metal part of a metal member, the calculating method comprising:

by using an analytical model in which a cut-surface is interpolated to the cross section of the metal member, the step of calculating a residual force vector that is a sum of a load vector acting on a first metal piece at the cut-surface and a load vector acting on a second metal piece at the cut-surface;

the step of calculating, as a modified displacement vector, an amount of movement at the cross section by interpolating the residual force vector as a forced load to the cross section of an analytical model of the metal member;

by using an analytical model having a shape of a cut-surface of the first metal piece obtained by cutting off the metal member at the cross section in such a way that the first metal part becomes the first metal piece or by using an analytical model having a shape of a cut-surface of the second metal piece obtained by cutting off the metal member at the cross section in such a way that the second metal part becomes the second metal piece, the step of modifying the shape of the cut-surface of the first metal piece or the shape of the cut-surface of the second metal piece on the basis of the calculated modified displacement vector; and by using the analytical model in which the shape of the cut-surface of the first metal piece is modified or the analytical model in which the shape of the cut-surface of the second metal piece is modified, the step of calculating a residual stress distribution at the cross section by interpolating a forced displacement to the analytical model.

The present invention also provides a program that enables a computer to execute the calculating method of the present invention.

Hereinafter, an Embodiment of the present invention will be described with reference to the accompanying drawings. Structures shown in the drawings or described below should be recognized as exemplifications in all respects, and the scope of the present invention is not limited to the drawings and the following descriptions.

FIG. 1 and FIG. 2 show explanatory diagrams of a residual stress distribution measuring method in accordance with the present Embodiment. FIG. 3 shows an analytical model of a metal member to be used for the residual stress distribution measuring method in accordance with the present Embodiment.

The measuring method in accordance with the present Embodiment is to measure a residual stress distribution at a cross section 7 between a first metal part 3 and a second metal part 4 of a metal member 2. The measuring method in accordance with the present Embodiment comprises:

the step of cutting the metal member 2 at the cross section 7 (cut-surface 8) in such a way that the first metal part 3 is cut off and becomes a first metal piece 5, and the second metal part is cut off and becomes a second metal piece;

the step of measuring a shape of a cut-surface 8*a* of the first metal piece or a shape of a cut-surface 8*b* of the second metal piece 6; by using an analytical model 10 in which a cut-surface 8 is interpolated to the cross section 7 of the metal member 2, the step of calculating a residual force vector that is a sum of a load vector acting on the first metal piece 5 at the cut-surface 8 and a load vector acting on the second metal piece 6 at the cut-surface 8;

the step of calculating, as a modified displacement vector 15, an amount of movement at the cross section 7 by interpolating the residual force vector as a forced load to the cross section 7 of an analytical model of the metal member 2;

by using an analytical model 12 having the shape of the cut-surface 8*a* of the measured first metal piece 5 or an analytical model 13 having the shape of the cut-surface 8*b* of the measured second metal piece 6, the step of modifying the shape of the cut-surface 8*a* of the first metal piece or the shape of the cut-surface 8*b* of the second metal piece 6 on the basis of the calculated modified displacement vector 15; and by using the analytical model 12 in which the shape of the cut-surface 8*a* of the first metal piece 5 is modified or the analytical model 13 in which the shape of the cut-surface 8*b* of the second metal piece 6 is modified, the step of calculating a residual stress distribution at the cross section 7 by interpolating a forced displacement to the analytical model 12 or 13.

The calculating method in accordance with the present Embodiment is to calculate the residual stress distribution at the cross section 7 between the first metal part 3 and the second metal part 4 of the metal member 2 by using the structural analysis by the finite element method. The calculating method in accordance with the present Embodiment comprises:

by using an analytical model 10 in which the cut-surface 8 is interpolated to the cross section 7 of the metal member 2, the step of calculating a residual force vector that is a sum of a load vector acting on the first metal piece 5 at the cut-surface 8 and a load vector acting on the second metal piece 6 at the cut-surface 8;

the step of calculating, as a modified displacement vector 15, an amount of movement at the cross section 7 by interpolating the residual force vector as a forced load to the cross section 7 of an analytical model of the metal member 2;

by using the analytical model 12 having the shape of the cut-surface 8*a* of the first metal piece 5 obtained by cutting off the metal member 2 at the cross section 7 in such a way that the first metal part 3 becomes the first metal piece 5 or by using the analytical model 13 having the shape of the cut-surface 8*b* of the second metal piece 6 obtained by cutting off the metal member 2 at the cross section 7 in such a way that the second metal part 4 becomes the second metal piece 6, the step of modifying the shape of the cut-surface 8*a* of the first metal piece 5 or the shape of the cut-surface 8*b* of the second metal piece 6 on the basis of the calculated modified displacement vector 15; and by using the analytical model 12 in which the shape of the cut-surface 8*a* of the first metal piece 5 is modified or the analytical model 13 in which the shape of the cut-surface 8*b* of the second metal piece 6 is modified, the step of calculating a residual stress distribution at the cross section 7 by interpolating a forced displacement to the analytical model 12 or 13.

The program in accordance with the present Embodiment is prepared in such a way as to enable the computer to execute the calculating method in accordance with the present Embodiment.

The metal member 2 is an object for a residual stress distribution measurement. Examples of the metal member 2 include weld materials, processed metal materials, and industrial components. The metal member 2 may have, for example, a welded welding line.

The measuring method in accordance with the present Embodiment may be used for a residual stress distribution measurement of, for example, a test-prepared metal member 2, a metal member 2 having a problem such as malfunction, or a metal member 2 optionally selected from a plurality of metal members 2 of the same type prepared.

The residual stress is a self-equilibrated stress that is present in the metal member 2. The residual stress is generated in the metal member during a process such as a weld process.

The measuring method in accordance with the present Embodiment is to measure residual stress distributions at the cross section 7 of the metal member 2. The cross section 7 is where the metal member 2 is cut off in such a way that the cut-surface 8 is formed at the cross section 7 and that the metal member 2 is divided into the first metal piece 5 and the second metal piece 6. The first metal piece 5 of the metal member 2 is comparable to the first metal part 3, and the second metal piece 6 of the metal member 2 is comparable to the second metal part 4. The cross section 7 is flat. Also, the cross section 7 can be configured in such a way as to intersect with the welding line. The cross section 7 can also be configured in such a way that the first metal part 3 and the second metal part 4 become asymmetric.

As shown in FIGS. 1(*a*) to 1(*c*), the metal member 2 having a welding line 20 is cut off at the cross section 7 (cut-surface 8) indicated by the dashed line A-A; and the metal member 2 is divided into the first metal piece 5 and the second metal piece 6. To cut off the metal member 2, for example, wire electrical discharge machining may be used.

By cutting off the metal member 2, a residual stress is released and re-divided at the cut-surface 8*a* of the first metal piece 5 and at the cut-surface 8*b* of the second metal piece 6, thereby causing an elastic deformation such that the cut-surfaces 8*a*, 8*b* become concave or convex. For example, a part of the cut-surfaces 8*a*, 8*b* where a tensile residual stress is generated at the cross section 7 becomes concave, while a part of the cut-surfaces 8*a*, 8*b* where a compressive residual stress is generated at the cross section 7 becomes convex.

Next, as shown in FIG. 1(*d*), a shape of the cut-surface 8*a* of the first metal piece 5 and a shape of the cut-surface 8*b* of the second metal piece 6 are measured by using a three-dimensional measuring device. The three-dimensional measuring device is, for example, a laser displacement meter, a three-dimensional coordinate measuring machine (CMM), or a non-contact photoscanner. The measured shape of the cut-surface 8*a* and the measured shape of the cut-surface 8*b* may be subjected to smoothing processing.

Next, an analytical model 10 of the metal member 2 is prepared by a finite element method (FEM). An element of the analytical model may have a cubic shape. A cut-surface 8 is interpolated to a cross section 7 of the prepared analytical model 10; and a residual force vector is calculated that is a sum of a load vector (reaction force) acting on the first metal piece 5 at the cut-surface 8 and a load vector (reaction force) acting on the second metal piece 6 at the cut-surface 8. The cut-surface 8 of this analytical model is not elastically deformed, and the cut-surface 8 of the first metal piece 5 and the cut-surface 8 of the second metal piece 6 are the same plane.

By interpolating, as a forced load, the calculated residual force vector to the cross section 7 of the analytical model 10 of the metal member 2, a movement amount at the cross section 7 is calculated as a modified displacement vector. The calculations of the residual force vector and the modified displacement vector will be described with use of FIGS. 2 and 3.

In FIG. 2, the first metal part 3 (the first metal piece 5) is assumed as a spring 26a ($l_1$ as a natural length and $k_1$ as a spring constant); and the second metal part 4 (the second metal piece 6) is assumed as a spring 26b ($l_2$ as a natural length and $k_2$ as a spring constant).

As shown in FIG. 2(a), one end of the spring 26a is fixed and the other end thereof is pulled by $u_1$, while one end of the spring 26b is fixed and the other end thereof is pulled by $u_2$, thereby allowing the springs 26a, 26b to come in contact with (but not adhere to) each other at a position 28a. In this case, a reaction force $F_1$ of the spring 26a at the position 28a becomes $k_1 u_1$, while a reaction force $F_2$ of the spring 26b becomes $k_2 u_2$. $F_1$ and $F_2$ at the position 28a are not equilibrated, resulting in $k_1 u_1 - k_2 u_2 = R$. This R is recognized as a residual force. $F_1$ and $F_2$ that are equilibrated result in $k_1 u_1 - k_2 u_2 = 0$.

An amount of movement $u^{mod}$ will be calculated that is from the position 28a, where $F_1$ and $F_2$ by the residual force R are not equilibrated, to the position 28b, where $F_1$ and $F_2$ are equilibrated. This movement amount becomes a modified displacement vector $u^{mod}$.

FIG. 2(b) shows that the spring 26a connects with the spring 26b, becoming one spring. A spring constant k of this spring is $k_1 + k_2$. A residual force R as a forced load is interpolated to the position 26a of this spring.

In this case, a relationship among an amount of movement $u^{mod}$ (modified displacement vector) at a position where the load is applied (the position 26a to the position 26b) and a spring constant k and a residual force R becomes $k \cdot u^{mod} = R$, resulting in $u^{mod} = R/(k_1 + k_2)$.

FIG. 2(c) shows that the obtained modified displacement vector $u^{mod}$ and $u_1$ or $u_2$ are summated, obtaining modified equilibrium positions $u_1'$ and $u_2'$ and thereby formulating equations calculated as follows:

$$u_1' = u_1 + u^{mod}$$

$$u_2' = u_2 - u^{mod}$$

In a case where such a theory is applied to the analytical model of the metal member 2, it makes it possible to modify the shape of the cut-surface 8a of the first metal piece 5 and the shape of the cut-surface 8b of the second metal piece 6 respectively into shapes supposed to be at a position where the reaction forces by the residual stress are equilibrated.

Next, an analytical model 10 of the metal member 2 is prepared like a welded flat metal plate as shown in FIG. 3.

The prepared analytical model 10 is fixed at both ends thereof in an X direction, and a cut-surface 8 is interpolated to a cross section 7 that divides the analytical model into a first metal part 3 and a second metal part 4 (the metal member 2 is divided into a first metal piece 5 and a second metal piece 6 at the cut-surface 8; however, a cut-surface 8a of the first metal piece 5 forcibly adheres to a cut-surface 8b of the second metal piece 6 at the cut-surface 8).

The first metal piece 5 and the second metal piece 6 each are then recognized to have a fixed boundary (fixed surface), a forced displacement boundary (cut-surface 8), and a free region where belongs to neither of the boundaries.

Equations of equilibrium inside the first metal piece 5 and the second metal piece 6 are represented by equation 1 and equation 2, respectively. K represents a rigid matrix, U represents a displacement vector, and F represents a load vector. The first metal piece 5 is accompanied with a superscript "1", and the second metal piece 6 is accompanied with a superscript "2".

Entries related to the fixed boundary are accompanied with a subscript "1" (a subscript "10" is an impact of the free region related to rigidity of the fixed boundary, a subscript "11" is the rigidity of the fixed boundary, and a subscript of "12" is an impact of the forced displacement boundary related to the rigidity of the fixed boundary); entries related to the forced displacement boundary are accompanied with a subscript "2" (a subscript "20" is an impact of the free region related to rigidity of the forced displacement boundary, a subscript "21" is an impact of the fixed boundary related to the rigidity of the forced displacement boundary, and a subscript "22" is the rigidity of the forced displacement boundary); and entries related to the free region other than the above boundaries are accompanied with a subscript "0" (a subscript "00" is rigidity of the free region, a subscript "01" is an impact of the fixed boundary related to the rigidity of the free region, and a subscript "02" is an impact of the forced displacement boundary related to the rigidity of the free region).

$$\begin{bmatrix} [K_{00}^1] & [K_{01}^1] & [K_{02}^1] \\ [K_{10}^1] & [K_{11}^1] & [K_{12}^1] \\ [K_{20}^1] & [K_{21}^1] & [K_{22}^1] \end{bmatrix} \begin{Bmatrix} \{U_0^1\} \\ \{U_1^1\} \\ \{U_2^1\} \end{Bmatrix} = \begin{Bmatrix} \{F_0^1\} \\ \{F_1^1\} \\ \{F_2^1\} \end{Bmatrix} \quad \text{Equation 1}$$

$$\begin{bmatrix} [K_{00}^2] & [K_{01}^2] & [K_{02}^2] \\ [K_{10}^2] & [K_{11}^2] & [K_{12}^2] \\ [K_{20}^2] & [K_{21}^2] & [K_{22}^2] \end{bmatrix} \begin{Bmatrix} \{U_0^2\} \\ \{U_1^2\} \\ \{U_2^2\} \end{Bmatrix} = \begin{Bmatrix} \{F_0^2\} \\ \{F_1^2\} \\ \{F_2^2\} \end{Bmatrix} \quad \text{Equation 2}$$

According to the equations of equilibrium, equation 1 and equation 2, the reaction forces exerted on the first metal piece 5 and the second metal piece 6 at the cut-surface 8 are represented by equation 3 and equation 4, respectively.

$$\{F_2^1\} = \begin{bmatrix} [K_{20}^1] & [K_{21}^1] & [K_{22}^1] \end{bmatrix} \begin{Bmatrix} \{U_0^1\} \\ \{U_1^1\} \\ \{U_2^1\} \end{Bmatrix} \quad \text{Equation 3}$$

$$\{F_2^2\} = \begin{bmatrix} [K_{20}^2] & [K_{21}^2] & [K_{22}^2] \end{bmatrix} \begin{Bmatrix} \{U_0^2\} \\ \{U_1^2\} \\ \{U_2^2\} \end{Bmatrix} \quad \text{Equation 4}$$

Therefore, a non-equilibrium force at the cut-surface 8, which is a residual force $\{R\}$, is $\{F_2^2\} + \{F_2^1\}$.

Next, the prepared analytical model 10 of the metal member 2 is fixed at both ends thereof in an X direction, and the calculated residual force as a forced load is interpolated to the cross section 7 (forced load boundary) where the first metal part 3 and the second metal part 4 are divided. Here, the metal member 2 is recognized as one member (i.e., the metal member is not cut off).

In this case, an equation of equilibrium inside the metal member 2 here is represented by equation 5. K represents a rigid matrix, U represents a displacement vector, and F represents a load vector. Entries related to the fixed boundary (fixed surface) are accompanied with a subscript "5" (a subscript "53" is an impact of the free region related to rigidity of the fixed boundary, a subscript "55" is the rigidity of the fixed boundary, and a subscript "54" is an impact of the forced load boundary related to the rigidity of the fixed boundary); entries related to the forced load boundary (cross section 7) are accompanied with a subscript "4" (a subscript "43" is an impact of the free region related to rigidity of the forced load boundary, a subscript "45" is an impact of the fixed boundary related to the rigidity of the forced load boundary, and a subscript "44" is the rigidity of the forced load boundary); and entries related to the free region other than the above boundaries are accompanied with a subscript "3" (a subscript "33" is rigidity of the free region, a subscript "35" is an impact of the fixed boundary related to the rigidity of the free region, and a subscript "34" is an impact of the forced load boundary related to the rigidity of the free region).

$$\begin{bmatrix}[K_{33}] & [K_{34}] & [K_{35}]\\ [K_{43}] & [K_{44}] & [K_{45}]\\ [K_{53}] & [K_{54}] & [K_{55}]\end{bmatrix}\begin{Bmatrix}\{U_3\}\\ \{U_4\}\\ \{U_5\}\end{Bmatrix}=\begin{Bmatrix}\{F_3\}\\ \{F_4\}\\ \{F_5\}\end{Bmatrix} \quad \text{Equation 5}$$

The residual force {R} is interpolated to the cross section 7, thereby being expressed by $\{F_4\}=\{R\}$. The modified displacement vector (movement amount) at the cross section 7 (forced load boundary) is represented by $\{U^{mod}\}$, being expressed by $\{U_4\}=\{U^{mod}\}$.

A known displacement vector $\{U_5\}$ and unknown displacement vectors $\{U_3\}$ and $\{U^{mod}\}$ are separately sorted, thereby obtaining equation 6 from equation 5.

$$\begin{bmatrix}[K_{33}] & [K_{34}]\\ [K_{43}] & [K_{44}]\end{bmatrix}\begin{Bmatrix}\{U_3\}\\ \{U^{mod}\}\end{Bmatrix}=\begin{Bmatrix}\{F_3\}\\ \{R\}\end{Bmatrix}-\begin{bmatrix}[K_{35}]\\ [K_{45}]\end{bmatrix}\{U_5\} \quad \text{Equation 6}$$

The displacement vector $\{U_5\}$ at the fixed boundary surface is 0, and a load vector $\{F_3\}$ at a region other than the fixed boundary and the load boundary is also 0, thereby formulating equation 7 calculated from equation 6.

$$\begin{Bmatrix}\{U_2\}\\ \{U^{mod}\}\end{Bmatrix}=\begin{bmatrix}[K_{32}] & [K_{34}]\\ [K_{43}] & [K_{44}]\end{bmatrix}^{-1}\begin{Bmatrix}\{0\}\\ \{R\}\end{Bmatrix} \quad \text{Equation 7}$$

The obtained modified displacement vector $\{U^{mod}\}$ and $\{U_2^1\}$ or $\{U_2^2\}$ are summated, obtaining modified equilibrium positions $\{U'_2^1\}$ and $\{U'_2^2\}$ and thereby formulating equations calculated as follows:

$$\{U'_2^1\}=\{U_2^1\}+\{U^{mod}\}$$

$$\{U_2^2\}=\{U_2^2\}-\{U^{mod}\}$$

By using $\{U^{mod}\}$ to modify the displacement vector $\{U_2^1\}$ of the forced displacement boundary (cut-surface 8) of the first metal piece 5 and the displacement vector $\{U_2^2\}$ of the forced displacement boundary (cut-surfaces 8) of the second metal piece 6, an equilibrium condition becomes satisfied at the forced displacement boundary (cut-surface 8).

Next, an analytical model 12 or an analytical model 13 is prepared—the analytical model 12 having the shape of the cut-surface 8a (having been subjected to the smoothing processing) of the first metal piece 5 measured using the three-dimensional measuring device and the analytical model 13 having the shape of the cut-surface 8b (having been subjected to the smoothing processing) of the second metal piece 6 measured using the three-dimensional measuring device—and the shape of the cut-surface 8a of the first metal piece 5 of the analytical model 12 or the shape of the cut-surface 8b of the second metal piece 6 of the analytical model 13 is modified based upon the calculated modified displacement vector $\{U^{mod}\}$. For example, as shown in FIGS. 1(e) and 1(f), the shape of the cut-surface 8a is modified into a shape of a cut-surface 8a'; and the shape of the cut-surface 8b is modified into a shape of a cut-surface 8b'. This enables the cut-surface shapes to be modified into equilibrated shapes.

Next, by using the analytical model 12 in which the shape of the cut-surface 8a of the first metal piece 5 is modified or the analytical model 13 in which the shape of the cut-surface 8b of the second metal piece 6 is modified, a residual stress distribution at the cross section 7 is calculated by interpolating a forced displacement to the analytical models 12, 13. For example, as shown in FIG. 1(f), the forced displacement is interpolated to the cut-surface 8a' and the cut-surface 8b'; and the shape of the cut-surface 8a' or the shape of the cut-surface 8b' is pushed back by an elasticity analysis to be flat like the cross section 7, with the result that a residual stress distribution 23 can be calculated, as shown in FIG. 1(g).

Simulation

An analytical model, as shown in FIG. 3, was prepared; and a residual stress distribution was calculated by an FEM analysis. For this simulation, a shape of the cut-surface 8a of the first metal piece 5 and a shape of the cut-surface 8b of the second metal piece 6 were used, both the shapes being calculated by the FEM analysis.

A material for the metal member 2 (the first metal piece 5 and the second metal piece 6) was SM490A; and the metal member 2 was 200 mm in length, 200 mm in width, and 12 mm in thickness. A midsection on a surface of the metal member 2 was subjected to bead-on-plate welding in a width direction. Heat-input conditions were as follows: an electric current of 300 A, an electric voltage of 32 V, a welding speed of 11.7 mm/sec, and a thermal efficiency of 0.8.

The prepared analytical model 10 is fixed at both ends thereof in an X direction, and the cut-surface 8 is interpolated to the cross section 7 that divides the analytical model into the first metal part 3 and the second metal part 4. The cross section 7 was arranged in such a way that a ratio between a length of the first metal part 3 and a length of the second metal part 4 in the X direction becomes 3:1.

A residual stress distribution at the cross section 7 was calculated by a contour method using such an analytical model.

FIGS. 4(a) and 4(c) show residual stress distributions calculated by a traditional contour method using the shape of the cut-surface 8a; and FIGS. 4(b) and 4(d) show residual stress distributions calculated by the traditional contour method using the shape of the cut-surface 8b. In the traditional contour method, it is premised that the shape of the cut-surface 8a and the shape of the cut-surface 8b are mirror-symmetrical; and the shape of the cut-surface 8a and the shape of the cut-surface 8b are averaged before being used. In the above-described simulation, however, the first metal part 3 and the second metal part 4 are asymmetric; and thus the shape of the cut-surface 8a and the shape of the cut-surface 8b are not mirror-symmetrical; therefore, the shapes of the cut-surfaces are not averaged to calculate residual stress distributions at the shape of the cut-surface 8a and the shape of the cut-surface 8b, respectively.

FIGS. 5(a) and 5(c) show residual stress distributions calculated by a modified contour method of the present invention using the shape of the cut-surface 8a that was modified based upon the calculated modified displacement vector $\{U^{mod}\}$; and FIGS. 5(b) and 5(d) show residual stress distributions calculated by the modified contour method of the present invention using the shape of the cut-surface 8b that was modified based upon the calculated modified displacement vector $\{U^{mod}\}$.

It was found from the residual stress distributions shown in FIG. 4 that were calculated by the traditional contour method that the residual stress distribution calculated by using the shape of the cut-surface 8a of the first metal piece 5 is greatly different from the residual stress distribution calculated by using the shape of the cut-surface 8b of the second metal piece 6. This may be due to the fact that the first metal piece 5 and the second metal piece 6 are asymmetric.

It was found from the residual stress distributions shown in FIG. that were calculated by the modified contour method of the present invention that the residual stress distribution calculated by using the shape of the cut-surface 8a of the first metal piece 5 is almost the same as the residual stress distribution calculated by using the shape of the cut-surface 8b of the second metal piece 6. This may be due to the fact that the shapes of the cut-surfaces 8a, 8b were modified by the modified displacement vector $\{U^{mod}\}$, and thus the unequilibrated elastic change was modified that was caused by the difference in the shape between the first metal piece 5 and the second metal piece 6.

Residual Stress Distribution Measurement of Real Structure

FIG. 6(a) shows a diagrammatic perspective view of a test object viewed from diagonally above that is used for a residual stress distribution measurement; and FIG. 6(b) shows a diagrammatic perspective view of the test object viewed from diagonally below.

The test object (metal member 2) is a simulated rotatable bearing to be used for a marine diesel engine, a marine propeller, or the like. The test object comprises a first metal plate (length: 240 mm; width: 170 mm; and thickness: 40 mm) with a 40-mm-diameter hole; a tubular metal member (thickness: 40 mm; outer diameter: 100 mm; and inner diameter: 54 mm) joined to an upper surface of the first metal plate by welding; and a second metal plate (length: 180 mm; width: 100 mm; and thickness: 40 mm) joined to a lower surface of the first metal plate by welding. The holes of the first and the second metal plates and the hole of the tubular metal member overlap and go through each other. A material for the test object is S25C. The first metal plate was joined to the tubular metal member by two passes of fillet welding. Also, the first metal plate was joined to the second metal plate by two passes of the fillet welding.

This test object (metal member 2) was cut off through the dashed line A-A by wire electrical discharge machining (wire diameter: 0.3 mm), and was divided into a first metal piece 5 and a second metal piece 6; and a shape of a cut-surface 8a of the first metal piece 5 and a shape of a cut-surface 8b of the second metal piece 6 were measured with a laser displacement meter. The measured shapes were subjected to smoothing processing.

An analytical model of the first metal piece 5 having the measured shape of the cut-surface 8a (having been subjected to the smoothing processing) and an analytical model of the second metal piece 6 having the measured shape of the cut-surface 8b (having been subjected to the smoothing processing) were prepared; and residual stress distributions at the cross section 7 were calculated by the traditional contour method or the modified contour method of the present invention.

FIG. 7(a) shows a residual stress distribution calculated based upon the elasticity analysis by the traditional contour method with use of the shape of the cut-surface 8a (having been subjected to the smoothing processing) of the first metal piece 5; and FIG. 7(b) shows a residual stress distribution calculated based upon the elasticity analysis by the traditional contour method with use of the shape of the cut-surface 8b (having been subjected to the smoothing processing) of the second metal piece 6. With the traditional contour method, the cut-surface shapes cannot be obtained by taking into account a difference in rigidity between the first metal piece 5 and the second metal piece 6; therefore, if the test object (metal member 2) is cut off asymmetrically, in the same way as in the measurement of the present invention, the shape of the cut-surface 8a and the shape of the cut-surface 8b cannot be averaged. For this reason, the shape of the cut-surface 8a measured from the first metal piece 5 as the forced displacement was interpolated to the cut-surface of the analytical model having the same size as the first metal piece 5, thereby measuring the residual stress distribution. The second metal piece 6 was subjected to the residual stress distribution measurement in the same way as above.

It was found from FIGS. 7(a) and 7(b) that if the metal member 2 was cut off asymmetrically, the residual stress distributions calculated by the traditional contour method were highly uneven. It was also found that the residual stress distribution calculated from the shape of the cut-surface 8a shown in FIG. 7(a) and the residual stress distribution calculated from the shape of the cut-surface 8b shown in FIG. 7(b) were not mirror-symmetrical and were discontinuous.

FIG. 8(a) shows a residual stress distribution calculated based upon the elasticity analysis by the modified contour method of the present invention with use of the shape of the cut-surface obtained by modifying the shape of the cut-surface 8a (having been subjected to the smoothing processing) of the first metal piece 5 based upon the modified displacement vector $\{U^{mod}\}$; and FIG. 8(b) shows a residual stress distribution calculated based upon the elasticity analysis by the modified contour method of the present invention with use of the shape of the cut-surface obtained by modifying the shape of the cut-surface 8b (having been subjected to the smoothing processing) of the second metal piece 6 based upon the modified displacement vector $\{U^{mod}\}$.

It was found from FIGS. 8(a) and 8(b) that, if the metal member 2 was cut off asymmetrically, the residual stress distributions calculated by the modified contour method of the present invention were smooth. It was also found that the residual stress distribution calculated from the shape of the cut-surface 8a shown in FIG. 8(a) and the residual stress distribution calculated from the shape of the cut-surface 8b shown in FIG. 8(b) were almost mirror-symmetrical and continuous.

In view of the above, the modified contour method of the present invention is capable of the residual stress measurement of the real structure that is asymmetrically divided into two at a given position in consideration of the difference in rigidity of every member.

REFERENCE SIGNS LIST

2: metal member
3: first metal part

4: second metal part
5: first metal piece
6: second metal piece
7: cross section
8, 8a, 8a', 8b, 8b': cut-surface
10: analytical model of metal member
12: analytical model of first metal piece
13: analytical model of second metal piece
15: modified displacement vector
20: welding line
21: three-dimensional measuring device
23: residual stress distribution
24: cutting device
26, 26a, 26b, 26c: spring
28a, 28b: position

The invention claimed is:

1. A measuring method for measuring a residual stress distribution at a cross section between a first metal part and a second metal part of a metal member, the measuring method comprising:
the step of cutting the metal member at the cross section in such a way that the first metal part is cut off and becomes a first metal piece, and the second metal part is cut off and becomes a second metal piece;
the step of measuring a shape of a cut-surface of the first metal piece or a shape of a cut-surface of the second metal piece;
by using an analytical model in which a cut-surface is interpolated to the cross section of the metal member, the step of calculating a residual force vector that is a sum of a load vector acting on the first metal piece at the cut-surface and a load vector acting on the second metal piece at the cut-surface;
the step of calculating, as a modified displacement vector, an amount of movement at the cross section by interpolating the residual force vector as a forced load to the cross section of an analytical model of the metal member;
by using an analytical model having the shape of the cut-surface of the measured first metal piece or an analytical model having the shape of the cut-surface of the measured second metal piece, the step of modifying the shape of the cut-surface of the first metal piece or the shape of the cut-surface of the second metal piece on the basis of the calculated modified displacement vector; and
by using the analytical model in which the shape of the cut-surface of the first metal piece is modified or the analytical model in which the shape of the cut-surface of the second metal piece is modified, the step of calculating a residual stress distribution at the cross section by interpolating a forced displacement to the analytical model.

2. The measuring method according to claim 1, wherein the step of calculating the residual stress distribution is the step of calculating the residual stress distribution at the cross section by interpolating the forced displacement to the analytical model by using an elasticity analysis.

3. A calculating method for calculating a residual stress distribution at a cross section between a first metal part and a second metal part of a metal member, the calculating method comprising:
by using an analytical model in which a cut-surface is interpolated to the cross section of the metal member, the step of calculating a residual force vector that is a sum of a load vector acting on a first metal piece at the cut-surface and a load vector acting on a second metal piece at the cut-surface;
the step of calculating, as a modified displacement vector, an amount of movement at the cross section by interpolating the residual force vector as a forced load to the cross section of an analytical model of the metal member;
by using an analytical model having a shape of a cut-surface of the first metal piece obtained by cutting off the metal member at the cross section in such a way that the first metal part becomes the first metal piece or by using an analytical model having a shape of a cut-surface of the second metal piece obtained by cutting off the metal member at the cross section in such a way that the second metal part becomes the second metal piece, the step of modifying the shape of the cut-surface of the first metal piece or the shape of the cut-surface of the second metal piece on the basis of the calculated modified displacement vector; and
by using the analytical model in which the shape of the cut-surface of the first metal piece is modified or the analytical model in which the shape of the cut-surface of the second metal piece is modified, the step of calculating a residual stress distribution at the cross section by interpolating a forced displacement to the analytical model.

4. The calculating method according to claim 3, wherein
the step of calculating the residual force vector is the step of calculating the residual force vector by using a structural analysis by a finite element method;
the step of modifying the shape of the cut-surface of the first or the second metal piece is the step of modifying the shape of the cut-surface of the first or the second metal piece by using the structural analysis by the finite element method; and
the step of calculating the residual stress distribution at the cross section is the step of calculating the residual stress distribution at the cross section by interpolating the forced displacement to the analytical model by using an elasticity analysis.

5. A non-transitory computer-readable medium storing a computer program for causing a computer processor to perform the calculating method according to claim 3.

* * * * *